US00PP14296P39

(12) United States Plant Patent

Murakami et al.

(10) Patent No.: US PP14,296 P3
(45) Date of Patent: Nov. 11, 2003

(54) VERBENA PLANT NAMED 'SUNVIVARE'

(50) Latin Name: *Verbena peruviana*
Varietal Denomination: Sunvivare

(75) Inventors: Yasuyuki Murakami, Shiga (JP); Yasunori Yomo, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/066,736

(22) Filed: Feb. 6, 2002

(65) Prior Publication Data

US 2003/0150039 P1 Aug. 7, 2003

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | |
|---|---|---|---|
| PP8,995 | P | 11/1994 | Tachibana et al. |
| PP9,014 | P | 12/1994 | Tachibana et al. |
| PP9,059 | P | 2/1995 | Tachibana et al. |
| PP9,085 | P | 3/1995 | Tachibana et al. |
| PP9,121 | P | 4/1995 | Tachibana et al. |
| PP9,411 | P | 12/1995 | Tachibana et al. |
| PP10,311 | P | 3/1998 | Tachibana |
| PP10,705 | P | 11/1998 | Tachibana |
| PP10,743 | P | 1/1999 | Nagase |
| PP10,755 | P | 1/1999 | Nagase |
| PP10,801 | P | 2/1999 | Nagase |
| PP11,037 | P | 8/1999 | Yomo et al. |
| PP11,104 | P | 10/1999 | Yomo et al. |
| PP11,113 | P | 11/1999 | Yomo et al. |
| PP11,120 | P | 11/1999 | Yomo et al. |
| PP11,130 | P | 11/1999 | Yomo et al. |

OTHER PUBLICATIONS

U.S. Plant patent application Ser. No. 375,362, which was abandoned in favor of continuation application No. 09/987,810 naming Yasunori Yomo and Kiyoshi Miyazaki as inventor(s) and filed on Nov. 16, 2001.
U.S. Plant patent application Ser. No. 375,408, which was abandoned in favor of continuation application No. 09/987,811 naming Yuki Watanabe and Ryuichi Tachibana as inventors and filed on Nov. 16, 2001.

*Primary Examiner*—Kent Bell
(74) *Attorney, Agent, or Firm*—Burns, Doane, Swecker & Mathis, L.L.P.

(57) ABSTRACT

Disclosed herein is a new and distinct variety of broadly spreading Verbena plant having a semi-erect growth habit with medium stems. The new Verbena plant has abundant branching particularly with respect to primary branching, and great profusion of blooms with the entire plant remaining in bloom for a considerable period of time. The flowers are large and the petals display a deep red color without an eye. The flowers are formed in profusion in a spike. The blooming period is from late April to November and the flowering duration is long. The plant exhibits high tolerance to cold, moderate tolerance to heat, high resistance to pests and diseases, particularly powdery mildew, and high resistance to rain.

3 Drawing Sheets

Botanical/commercial classification: *Verbena peruviana*/Verbena Plant.
Varietal denomination: cv. 'Sunvivare'.

BACKGROUND OF THE VARIETY

The present invention relates to a new and distinct variety of Verbena plant obtained as a mutation of *Verbena peruviana* variety 'Sunvivaro' (U.S. Plant Pat. No. 13,724, filed Nov. 16, 2001).

The Verbena is a very popular plant and is used for flower bedding and potting in the summer season. There are only a few varieties of the Verbena plant which have abundant branching, many deep red flowers in a spike, a long flowering duration, and a high resistance to cold, rain, diseases and pests. Accordingly, this invention is aimed at obtaining a new variety having much branching, many flowers in a spike, a long flowering duration, a high resistance to cold, rain, diseases and pests, and moderate resistance to heat.

The new variety was discovered as a spontaneous branch mutation in August 1998 while growing in a field in Germany. The mutant Verbena plant was propagated by the use of cuttings and was grown in trials beginning in May 1999 in the Yamanashi and Shiga prefectures of Japan. The botanical characteristics of the plant were examined, using a similar 'Sunvivaro' variety and the 'Sunvivapa' variety (U.S. Plant patent application Ser. No. 09/987,811, filed Nov. 16, 2001) for comparison. As a result, it was concluded that this Verbena plant is distinguishable from other varieties whose existence is known to us. The new variety of the present invention has been named 'Sunvivare'.

In the following description, the color-coding is in accordance with The R.H.S. Colour Chart of The Royal Horticultural Society, London, England. The Japan Color Standard for Horticultural Plant (J.H.S. Color Chart) is also added for reference.

The main botanical characteristics of the parent 'Sunvivaro' variety are as follows:

Plant:
- *Growth habit.*—Erect.
- *Width.*—Medium.
- *Height.*—Medium to high.

Stem:
- *Diameter.*—Medium (approximately 1.4–3.0 mm).
- *Anthocyanin pigmentation.*—Absent.

*Pubescence.*—Medium.
*Prickles.*—Absent.
*Branching.*—Medium.
*Subterranean stem.*—Absent.
*Length of internode.*—Short (approximately 1.0–1.8 cm).

Leaf:
*Phyllotaxis.*—Opposite.
*Shape of blade.*—Hastate.
*Blade incision.*—Present.
*Depth of blade incision.*—Shallow.
*Blade crenation of margin.*—Serrate.
*Length.*—Medium (approximately 3.8 cm).
*Width.*—Medium (approximately 2.5 cm).
*Color.*—Grayish olive green (R.H.S. Colour Chart No. 137A, J.H.S. Color Chart No. 3716).
*Pubescence.*—Sparse.
*Petiole.*—Present.
*Diameter of petiole.*—Medium (approximately 1.8 mm).
*Length of petiole.*—Short (approximately 2.6 mm).

Flower:
*Shape of cluster.*—Funnel-shaped.
*Length of cluster.*—Medium (approximately 31 mm).
*Diameter of cluster.*—Medium to large (approximately 45–54 mm).
*Facing direction.*—Upward.
*Outward curvature of petal.*—Slightly curved.
*Diameter.*—Large (approximately 1.8–2.2 cm).
*Length.*—Medium.
*Color.*—Vivid purplish red (R.H.S. Colour Chart No. 66A, J.H.S. Color Chart No. 9707).
*Eye color.*—Absent.
*Variegation on petals.*—Absent.
*Color intensity.*—Substantially even.
*Incision of petal.*—Present.
*Number of petals.*—Medium 4.
*Incision of calyx.*—Present.
*Length of calyx.*—Long (approximately 1.2 mm).
*Anthocyanin pigmentation of calyx limb.*—Absent.
*Shape of pistil.*—Two lobes.
*Number of stamens.*—Medium.
*Color of anther.*—Yellowish green.
*Diameter of peduncle.*—Thin (approximately 1.2 mm).
*Length of peduncle.*—Long (approximately 1.3 cm).
*Number of flowers.*—Many.
*Reproductive organs.*—1 pistil and 4 stamens.
*Flower fragrance.*—Absent.
*Flowering time.*—Medium.
*Flowering duration.*—Long.

Physiological and ecological characteristics: High resistance to diseases and pests, particularly powdery mildew. High tolerance to cold and rain. Moderate tolerance to heat.

The main botanical characteristics of 'Sunvivapa' variety are as follows:

Plant:
*Growth habit.*—Erect.
*Plant width.*—Medium (approximately 60 cm).
*Plant height.*—High (approximately 40–50 cm).

Stem:
*Diameter.*—Medium (approximately 2–3 mm).
*Anthocyanin pigmentation.*—Present.
*Pubescence.*—Dense.
*Prickles.*—Absent.
*Branching.*—Abundant.
*Subterranean stem.*—Absent.
*Length of internode.*—Medium (approximately 4–5 cm).

Leaf:
*Phyllotaxis.*—Opposite.
*Shape of blade.*—Hastate.
*Blade incision.*—Present.
*Depth of blade incision.*—Shallow.
*Crenation of blade margin.*—Crenated.
*Length.*—Medium (approximately 4–5 cm).
*Width.*—Medium (approximately 3 cm).
*Color.*—Medium olive green (R.H.S. Colour Chart No. 146A, J.H.S. Color Chart No. 3509).
*Pubescence.*—Medium.
*Petiole.*—Present.
*Petiole diameter.*—Medium (approximately 1.5 mm).
*Petiole length.*—Medium (approximately 5.0 mm).

Flower:
*Shape of cluster.*—Funnel-shaped.
*Cluster length.*—Medium (approximately 3 cm).
*Cluster diameter.*—Large (approximately 4–5 cm).
*Facing direction.*—Upward.
*Outward curvature of petal.*—Slightly curved.
*Diameter.*—Large (approximately 20–30 mm).
*Length.*—Medium (approximately 1.5 cm).
*Color of petal.*—Vivid reddish purple (R.H.S. Colour Chart No. 78A, J.H.S. Color Chart No. 8907).
*Eye color.*—Absent.
*Variegation.*—Absent.
*Incision of petal.*—Present.
*Number of petals.*—Medium 5.
*Calyx incision.*—Present.
*Calyx length.*—Medium (approximately 1.3 cm).
*Anthocyanin pigmentation of calyx limb.*—Present.
*Shape of pistil.*—Two lobes.
*Number of stamens.*—Medium.
*Color of anther.*—Yellowish green.
*Peduncle diameter.*—Medium (approximately 2.0 cm).
*Peduncle length.*—Medium (approximately 2.0 cm).
*Number of flowers.*—Medium.
*Reproductive organs.*—1 pistil and 4 stamens.
*Flower fragrance.*—Absent.
*Flowering time.*—Late.
*Flowering duration.*—Long.

Physiological and ecological characteristics:
*Tolerance to cold.*—High.
*Tolerance to heat.*—High.
*Resistance to diseases.*—High.
*Resistance to pests.*—High.

This new variety of Verbena plant 'Sunvivare' was asexually reproduced by the use of cuttings at Youkaichi-shi, Shiga-ken, Japan and Kitakoma-gun, Yamanashi-ken, Japan, and the homogeneity and stability thereof were confirmed. The new variety has been found to reproduce true to type in subsequent generations when asexually reproduced.

SUMMARY OF THE VARIETY

This new Verbena variety has a semi-erect growth habit and is tall. The plant has much branching and an abundant number of flowers in a spike with a great profusion of blooms. The blooming period is from late April to November, the flowers commonly remain open in the rainy season, and the flowering duration is long. The entire plant remains in bloom for a considerable period of time. The flower size is large and the petal color of the flowers is deep red in the absence of an eye. The plant is highly tolerant to cold, moderately tolerant to heat, and has high resistance to pests and diseases, particularly powdery mildew, and high resistance to rain.

It commonly takes approximately 12 weeks to produce a finished plant of the new variety following the rooting of a cutting.

BRIEF DESCRIPTION OF THE PHOTOGRAPHS

Figure 1:
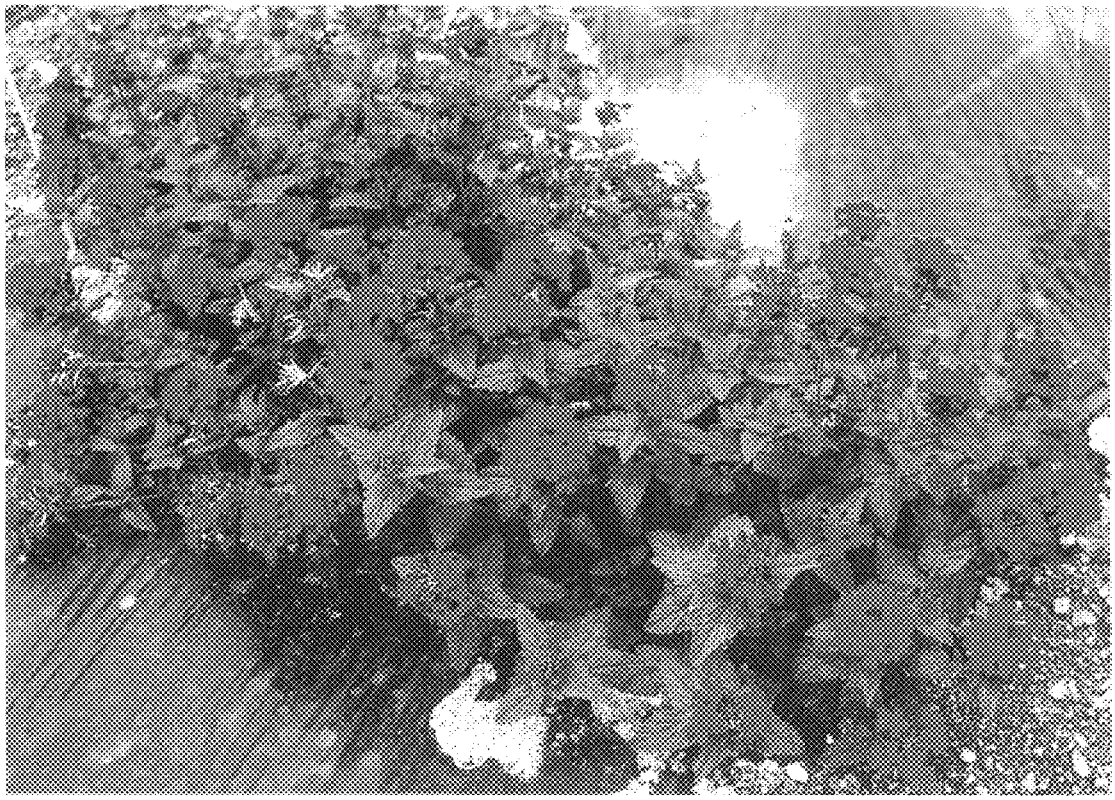
FIG. 1 shows a close overall view of plants of the new Verbena variety while growing in the ground.
Figure 2:
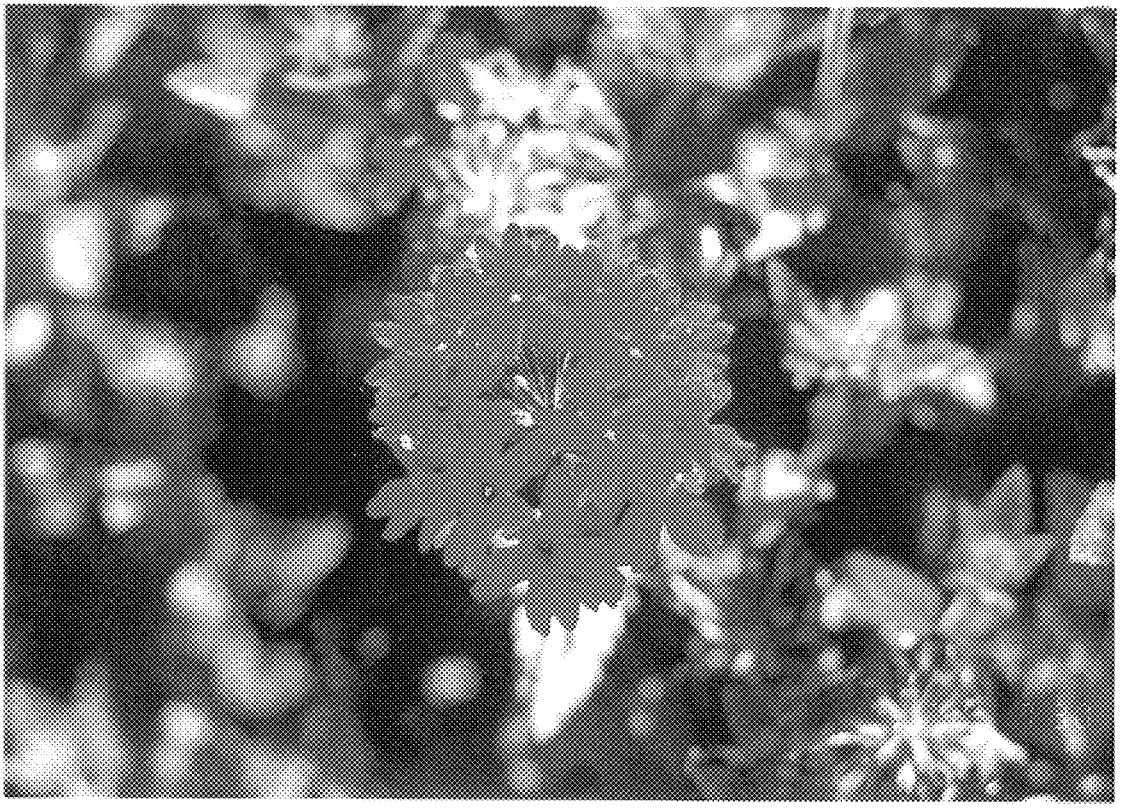
FIG. 2 shows a flower of the new variety of Verbena plant.
Figure 3:
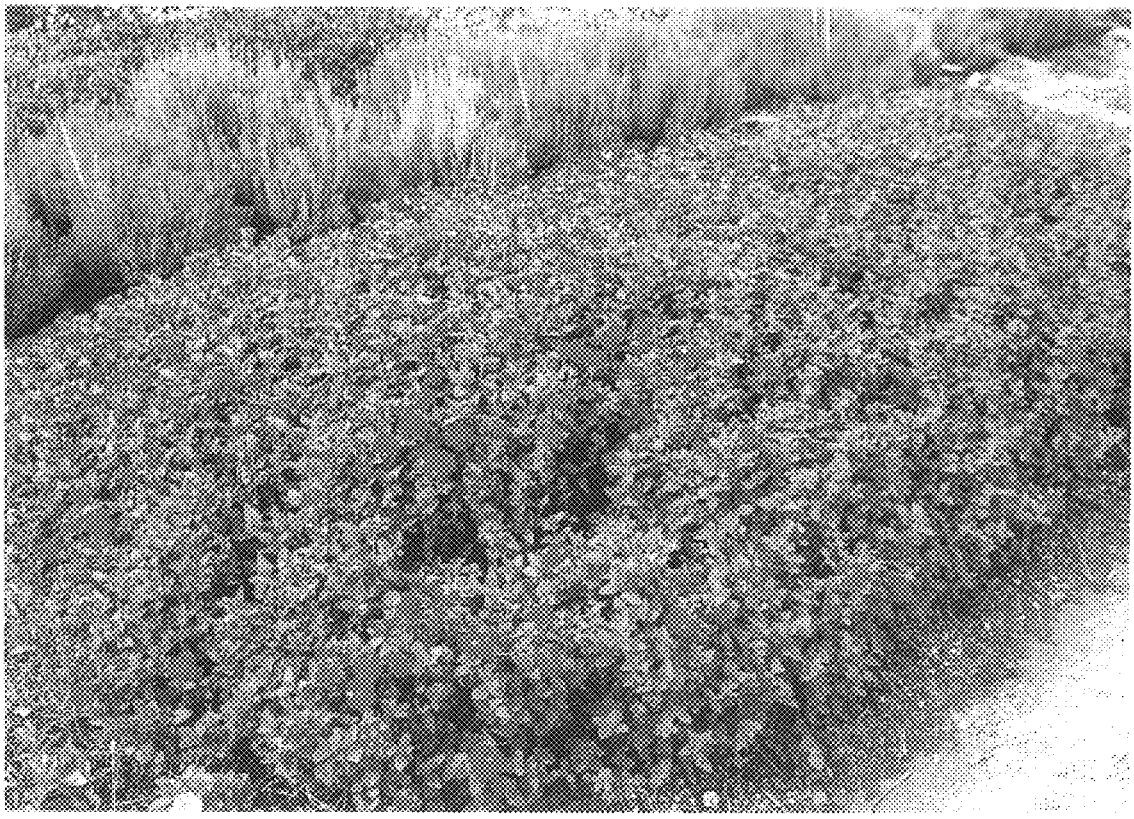
FIG. 3 shows a mass of plants of the new variety of the new Verbena variety while growing in the ground.

The age of the plants is approximately four months.

DESCRIPTION OF THE NEW VARIETY

The botanical characteristics of the new and distinct 'Sunvivare' variety are specified hereafter when observed during October at Youkaichi-shi, Shiga-ken, Japan. The plants had been asexually reproduced by the use of cuttings and were growing in 30 cm pots during the preceding April.

Plant:
- *Growth habit.*—Semi-erect.
- *Plant width.*—Broad (approximately 70 cm).
- *Plant height.*—High (approximately 30 cm).

Stem:
- *Diameter.*—Medium (approximately 2.8 mm).
- *Length.*—Approximately 3.6 cm.
- *Anthocyanin pigmentation.*—Absent.
- *Pubescence.*—Medium to dense.
- *Prickles.*—Absent.
- *Branching.*—Medium.
- *Subterranean stem.*—Absent.
- *Length of internode.*—Medium (approximately 3.6 cm).

Leaf:
- *Phyllotaxis.*—Opposite.
- *Shape of blade.*—Hastate.
- *Apex shape.*—Obtuse.
- *Base shape.*—Truncate.
- *Blade incision.*—Present.
- *Depth of blade incision.*—Shallow.
- *Blade margin.*—Serrate.
- *Length.*—Medium (approximately 4.1 cm).
- *Width.*—Medium (approximately 2.9 cm).
- *Color.*—Medium olive green (R.H.S. Colour Chart No. 137B, J.H.S. Color Chart No. 3508) on the upper surface, and R.H.S. Colour Chart No. 137C on the under surface.
- *Venation pattern.*—Dichotomous.
- *Pubescence.*—Medium.
- *Petiole.*—Present.
- *Petiole diameter.*—Medium (approximately 1.3 mm).
- *Petiole length.*—Short (approximately 1.8 mm).
- *Petiole color.*—R.H.S. Colour Chart No. 137B.

Flower:
- *Bud length.*—*Approximately* 1.1 to 1.5 cm.
- *Bud diameter.*—Approximately 1.2 to 1.5 mm.
- *Bud shape.*—Generally tubular.
- *Bud color.*—R.H.S. Colour Chart No. 137D.
- *Shape of cluster.*—Funnel-shaped.
- *Cluster length.*—Medium (approximately 30 mm).
- *Cluster diameter.*—Medium (approximately 50 mm).
- *Facing direction.*—Upward.
- *Outward curvature of petal.*—Slightly curved.
- *Diameter.*—Large (approximately 18 mm).
- *Length.*—Low (approximately 15 mm).
- *Color of petal.*—Deep red (R.H.S. Colour Chart No. 60A, J.H.S. Color Chart No. 0408) on the upper surface, and R.H.S. Colour Chart No. 70A on the under surface.
- *Eye color.*—Absent.
- *Variegation.*—Absent.
- *Petal apex.*—Rounded with a notch.
- *Petal base.*—Tubular.
- *Petal texture.*—Smooth.
- *Incision of petal.*—Present.
- *Number of petals.*—Medium (5).
- *Calyx incision.*—Present.
- *Calyx length.*—Long (approximately 1.0 cm).
- *Calyx shape.*—Possesses one tubular sepal having an acute apex and a rounded base.
- *Calyx color.*—R.H.S. Colour Chart No. 138A on the upper surface, and R.H.S. Colour Chart No. 138B on the under surface.
- *Anthocyanin pigmentation of calyx limb.*—Absent.
- *Pistil shape.*—Single and possesses two lobes.
- *Stamen number.*—Commonly four.
- *Anther color.*—Yellow green R.H.S. Colour Chart No. 1B.
- *Filament color.*—R.H.S. Colour Chart No. 1B.
- *Pollen color.*—R.H.S. Colour Chart No. 1B.
- *Stigma color.*—R.H.S. Colour Chart No. 4D.
- *Style color.*—R.H.S. Colour Chart No. 144B.
- *Ovaries.*—Commonly four in number.
- *Peduncle diameter.*—Thin (approximately 1.6 mm).
- *Peduncle length.*—Short (approximately 3.4 cm).
- *Peduncle color.*—R.H.S. Colour Chart No. 137C.
- *Number of flowers.*—Abundant, and commonly approximately 10 per spike.
- *Reproductive organs.*—1 pistil and 5 stamens.
- *Flower fragrance.*—Absent.
- *Flowering period.*—Commonly begins in April and ends in about November.
- *Flowering longevity.*—An individual bloom commonly lasts approximately 5 to 7 days on the plant and varies with environmental conditions.

Physiological and ecological characteristics:
- *Tolerance to cold.*—High, and has withstood a temperature of 4° F.
- *Tolerance to heat.*—Medium.
- *Resistance to diseases.*—High.
- *Resistance to pests.*—High.

This new variety of Verbena plant is most suitable for use in flower beds and for potting, particularly in hanging baskets and in planters, and is further excellent for use as a ground cover. Pinching of old blossoms will enhance the formation of new blossoms.

We claim:

1. A new and distinct variety of Verbena plant, substantially as herein illustrated and described, characterized particularly as to novelty by (A) a semi-erect growth habit, (B) a plentiful amount of flowers in a spike with a great profusion of blooms with the entire plant remaining in bloom for a considerable period of time, (C) a long flowering duration, (D) flowers that are of a large size having a petal color that is deep red without an eye, (E) a high resistance to rain, cold, drought, diseases and pests, and moderate resistance to heat, and (F) an early flowering time.

* * * * *